(12) United States Patent
Lederman

(10) Patent No.: US 11,998,516 B2
(45) Date of Patent: Jun. 4, 2024

(54) METHODS AND COMPOSITIONS FOR TREATING DEPRESSION USING CYCLOBENZAPRINE

(75) Inventor: Seth Lederman, South Dartmouth, MA (US)

(73) Assignee: TONIX PHARMA HOLDINGS LIMITED, Dublin (IE)

( * ) Notice: Subject to any disclaimer, the term of this patent is extended or adjusted under 35 U.S.C. 154(b) by 0 days.

(21) Appl. No.: 13/412,571

(22) Filed: Mar. 5, 2012

(65) Prior Publication Data

US 2012/0232159 A1  Sep. 13, 2012

Related U.S. Application Data

(60) Provisional application No. 61/449,838, filed on Mar. 7, 2011.

(51) Int. Cl.
*A61K 31/137* (2006.01)
*A61K 45/06* (2006.01)

(52) U.S. Cl.
CPC ............ *A61K 31/137* (2013.01); *A61K 45/06* (2013.01)

(58) Field of Classification Search
CPC .................................................. A61K 31/137
See application file for complete search history.

(56) References Cited

U.S. PATENT DOCUMENTS

| | | | |
|---|---|---|---|
| 3,882,246 A | 5/1975 | Share | |
| 4,968,507 A | 11/1990 | Zentner et al. | |
| 5,073,543 A | 12/1991 | Marshall et al. | |
| 5,120,548 A | 6/1992 | McClelland et al. | |
| 5,439,686 A | 8/1995 | Desai et al. | |
| 5,498,421 A | 3/1996 | Grinstaff et al. | |
| 5,591,731 A | 1/1997 | Kennedy et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,096,331 A | 8/2000 | Desai et al. | |
| 6,248,363 B1 | 6/2001 | Patel et al. | |
| 6,267,985 B1 | 7/2001 | Chen et al. | |
| 6,309,663 B1 | 10/2001 | Patel et al. | |
| 6,358,944 B1* | 3/2002 | Lederman et al. ........... | 514/220 |
| 6,383,471 B1 | 5/2002 | Chen et al. | |
| 6,395,788 B1* | 5/2002 | Iglehart, III ................. | 514/654 |
| 6,506,405 B1 | 1/2003 | Desai et al. | |
| 6,537,579 B1 | 3/2003 | Desai et al. | |
| 6,541,523 B2 | 4/2003 | Iglehart | |
| 6,649,186 B1 | 11/2003 | Robinson | |
| 6,720,001 B2 | 4/2004 | Chen et al. | |
| 6,749,868 B1 | 6/2004 | Desai et al. | |
| 6,753,006 B1 | 6/2004 | Desai et al. | |
| 6,761,903 B2 | 7/2004 | Chen et al. | |
| 7,105,486 B2 | 9/2006 | Mickle et al. | |
| 7,223,735 B2 | 5/2007 | Mickle et al. | |
| 7,532,935 B2 | 5/2009 | Maschino | |
| 7,655,630 B2 | 2/2010 | Mickle et al. | |
| 7,658,945 B2 | 2/2010 | Singh | |
| 7,659,253 B2 | 2/2010 | Mickle et al. | |
| 7,659,254 B2 | 2/2010 | Mickle et al. | |
| 7,662,787 B2 | 2/2010 | Mickle et al. | |
| 7,662,788 B2 | 2/2010 | Mickle et al. | |
| 7,671,030 B2 | 3/2010 | Mickle et al. | |
| 7,671,031 B2 | 3/2010 | Mickle et al. | |
| 7,674,774 B2 | 3/2010 | Mickle et al. | |
| 7,678,770 B2 | 3/2010 | Mickle et al. | |
| 7,678,771 B2 | 3/2010 | Mickle et al. | |
| 7,682,628 B2 | 3/2010 | Singh | |
| 7,687,466 B2 | 3/2010 | Mickle et al. | |
| 7,687,467 B2 | 3/2010 | Mickle et al. | |
| 7,700,561 B2 | 4/2010 | Mickle et al. | |
| 7,713,936 B2 | 5/2010 | Mickle et al. | |
| 7,718,619 B2 | 5/2010 | Mickle et al. | |
| 7,723,305 B2 | 5/2010 | Mickle et al. | |
| RE41,884 E | 10/2010 | Garavilla et al. | |
| 7,820,788 B2 | 10/2010 | Desai et al. | |
| 7,923,536 B2 | 4/2011 | Desai et al. | |
| 8,093,300 B2 | 1/2012 | Lederman | |
| 8,137,734 B2 | 3/2012 | Venkatesh et al. | |
| 8,138,229 B2 | 3/2012 | Desai et al. | |
| 8,216,610 B2 | 7/2012 | Roberts | |
| 8,586,103 B2 | 11/2013 | Li | |
| 8,688,385 B2 | 4/2014 | Mrazek et al. | |

(Continued)

FOREIGN PATENT DOCUMENTS

EP  2233134  9/2010
FR  2635461  2/1990

(Continued)

OTHER PUBLICATIONS

Godfrey, "A Guide to the Understanding and Use of Tricyclic Antidepressants in the Overall Management of Fibromyalgia and Other Chronic Pain Syndromes", Arch.Intern.Med., 1996, vol. 156, pp. 1047-1052.*
Arnold et al. "Antidepressant Treatment of Fibromyalgia", Psychosomatics, 2000, vol. 41, No. 2, pp. 104-113.*
Krishnan et al. "The molecular neurobiology of depression", Nature, 2008, vol. 455, No. 7215, pp. 894-902.*
Santandrea et al. "A Double-blind Crossover Study of Two Cyclobenzaprine Regimens in Primary Fibromyalgia Syndrome", J.Int.Med.Res., 1993, vol. 21, pp. 74-80.*
Aaronson et al., "Defining and measuring fatigue," Image J. Nurs. Sch., 31:45-50 (1999).

(Continued)

*Primary Examiner* — Kevin E Weddington

(74) *Attorney, Agent, or Firm* — HALEY GUILIANO LLP; James F. Haley, Jr.; Stacey W. Chung

(57) ABSTRACT

The present invention relates to methods for the treatment or prevention of depression, and related pharmaceutical compositions. Of particular interest are pharmaceutical compositions comprising cyclobenzaprine, alone, or in combination with an antidepressant drug.

6 Claims, No Drawings

(56) References Cited

U.S. PATENT DOCUMENTS

| | | | |
|---|---|---|---|
| 9,474,728 B2 | 10/2016 | Lederman et al. |
| 9,636,408 B2 | 5/2017 | Nebuloni |
| 9,918,948 B2 | 3/2018 | Lederman |
| 9,956,188 B2 | 5/2018 | Nebuloni |
| 10,117,936 B2 | 11/2018 | Nebuloni et al. |
| 10,322,094 B2 | 6/2019 | Nebuloni |
| 10,357,465 B2 | 7/2019 | Lederman |
| 10,722,478 B2 | 7/2020 | Lederman |
| 10,736,859 B2 | 8/2020 | Nebuloni |
| 10,864,175 B2 | 12/2020 | Nebuloni |
| 10,864,176 B2 | 12/2020 | Nebuloni |
| 11,026,898 B2 | 6/2021 | Lederman |
| 11,737,991 B2 | 8/2023 | Nebuloni et al. |
| 11,826,321 B2 | 11/2023 | Harris et al. |
| 11,839,594 B2 | 12/2023 | Nebuloni et al. |
| 2003/0077227 A1 | 4/2003 | Dugger |
| 2003/0077297 A1 | 4/2003 | Chen et al. |
| 2005/0059656 A1 | 3/2005 | Kristal |
| 2005/0096327 A1 | 5/2005 | Caprathe et al. |
| 2005/0181041 A1 | 8/2005 | Goldman |
| 2005/0203191 A1 | 9/2005 | McDonald |
| 2006/0073189 A1 | 4/2006 | Pinney et al. |
| 2007/0141144 A1 | 6/2007 | Roberts et al. |
| 2007/0196364 A1 | 8/2007 | Krishnamurthy |
| 2008/0146672 A1 | 6/2008 | Denton et al. |
| 2009/0054403 A1 | 2/2009 | Woiwode et al. |
| 2009/0069267 A1 | 3/2009 | Abrams |
| 2009/0098200 A1 | 4/2009 | Krayz et al. |
| 2009/0275541 A1 | 11/2009 | Sullivan |
| 2010/0021507 A1 | 1/2010 | Bunick et al. |
| 2010/0098832 A1 | 4/2010 | Venkatesh et al. |
| 2010/0247586 A1 | 9/2010 | Hugerth |
| 2010/0247649 A1 | 9/2010 | Palaparthi et al. |
| 2010/0266682 A1 | 10/2010 | Davar et al. |
| 2011/0068511 A1 | 3/2011 | Sowden et al. |
| 2011/0062614 A1 | 5/2011 | Suenaga |
| 2011/0124656 A1 | 5/2011 | Lederman et al. |
| 2011/0319389 A1 | 12/2011 | Lederman et al. |
| 2012/0101154 A1 | 4/2012 | Lederman et al. |
| 2012/0232159 A1 | 9/2012 | Lederman |
| 2013/0165511 A1 | 6/2013 | Lederman et al. |
| 2014/0171515 A1 | 6/2014 | Lederman |
| 2014/0336264 A1 | 11/2014 | Nebuloni |
| 2016/0030576 A1 | 2/2016 | Nebuloni |
| 2017/0065538 A1 | 3/2017 | Lederman |
| 2017/0239195 A1 | 8/2017 | Nebuloni |
| 2017/0281568 A1 | 10/2017 | Lederman |
| 2018/0193288 A1 | 7/2018 | Lederman |
| 2018/0344668 A1 | 12/2018 | Nebuloni |
| 2019/0022030 A1 | 1/2019 | Nebuloni |
| 2019/0022031 A1 | 1/2019 | Nebuloni |
| 2019/0175525 A1 | 6/2019 | Harris |
| 2019/0282517 A1 | 9/2019 | Nebuloni |
| 2019/0336458 A1 | 11/2019 | Lederman |
| 2019/0358177 A1 | 11/2019 | Lederman |
| 2021/0038538 A1 | 2/2021 | Nebuloni |
| 2021/0128495 A1 | 5/2021 | Lederman et al. |
| 2023/0414536 A1 | 12/2023 | Lederman et al. |

FOREIGN PATENT DOCUMENTS

| | | |
|---|---|---|
| WO | WO-1999018937 | 4/1999 |
| WO | WO-1999058115 | 11/1999 |
| WO | WO 2001/012174 | 2/2001 |
| WO | WO 2001/012175 | 2/2001 |
| WO | WO-2001089476 | 11/2001 |
| WO | WO-2004035021 | 4/2004 |
| WO | WO 2004/039320 | 5/2004 |
| WO | WO2005/051297 | 6/2005 |
| WO | WO-2007038620 | 4/2007 |
| WO | WO2008137923 | 11/2008 |
| WO | WO 2009/002770 | 12/2008 |
| WO | WO 2009/089494 | 7/2009 |
| WO | WO-2011062614 | 5/2011 |
| WO | WO2012137054 | 10/2012 |
| WO | WO2013188847 | 12/2013 |
| WO | WO2014071134 | 5/2014 |
| WO | WO-2014145156 | 9/2014 |
| WO | WO2016011451 | 1/2016 |

OTHER PUBLICATIONS

Abd el-Fattah et al., "Enhancement of dissolution rate of hydrochlorothiazide via solid dispersion," Pharmazie., 41:790-793 (1986).

Abernethyl et al., "Absolute bioavailability of imipramine: influence of food," Psychopharmacology (Berl.), 83:104-106 (1984).

Amin et al., "Indion 414 as superdisintegrant in formulation of mouth dissolve tablets," Indian Journal of Pharmaceutical Sciences, 68:117-119 (2006).

Amitai et al., "Distribution of amitriptyline and nortriptyline in blood: role of alpha-1-glycoprotein," Ther. Durg Monit., 15:267-273 (1993).

Bagul, Current Status of Table Disintegrants: A Review, retrieved from [http://www.pharmainfo.net/reviews/current-status-tablet-disintegrantsa-review].

Balant et al., "Prodrugs for the Improvement of Drug Absorption Via Different Routes of Administration," Eur. J. Drug Metab. Pharmacokinet, 15:143-153 (1990).

Balasubramaniam et al., "Effects of superdisintegrants on dissolution of cationic drugs," Dissolution Technologies, 18-25 (2008).

Barker and Blakely, "Identification of a single amino acid, phenylalanine 586, that is responsible for high affinity interactions of tricyclic antidepressants with the human serotonin transporter," Mol. Pharmacol., 50:957-965 (1996).

Barnes et al., "Brainstem noradrenergic system depression by cyclobenzaprine," Neuropharmacology, 19:221-224 (1980).

Bartoli et al., "An atypical case of reverse Takotsubo cardiomyopathy during general anesthesia in a 30-year-old male with post-traumatic stress disorder," J. Cardiothorac Vasc. Anesth., 25:1116-1118 (2011).

Baumann et al., "Amitriptyline pharmacokinetics and clinical response: I. Free and total plasma amitriptyline and nortriptyline," Int. Clin. Psychopharmacol., 1:89-101 (1986).

Bennett et al., "A comparision of cyclobenzaprine and placebo in the management of fibrositis: A double-blind controlled study," Arthritis Rheum., 31:1535-1542 (1988).

Berezhkovskiy, "Prediction of the possibility of the second peak of drug plasma concentration time curve after iv bolus administration from the standpoint of the traditional multi-compartmental linear pharmacokinetics," J. Pharm. Sci., 97:2385-2393 (2008).

Bhatt et al., "Development and validation of amitriptyline and its metabolite in human plasma by ultra performance liquid chromatography-tandem mass spectrometry and its application to a bioequivalence study," Biomedical Chromatography, 24:1247-1254 (2010).

Bhowmik et al., "Fast Dissolving Tablet: An Overview," Journal of Chemical and Pharmaceutical Research, 1:163-177 (2009).

Bi et al., "Mechanism of eutectic formation upon compaction and its effects on tablet properties," Thermochimica Acta, 404:213-226 (2003).

Bickel et al., "Buccal absorption and other properties of pharmacokinetic importance of imipramine and its metabolites," J. Pharm. Pharmacol., 21:160-168 (1969).

Blake et al., "The development of a clinician-administered PTSD scale," Journal of Traumatic Stress, 8:75-90 (1995).

Braithwaite et al., "Plasma concentration of amitriptyline and clinical response," Lancet., 17:1297-1300 (1972).

Breyer-Pfaff et al., "Comparative N-glucuronidation kinetics of ketotifen and amitriptyline by expressed human UDP-glucuronosyltransferases and liver microsomes," Drug Metab. Dispos., 28:869-872 (2000).

Brittain, "A summary of the scholarly activities associated with Center for Pharmaceutical Physics," Journal of Pharmaceutical Physics, vol. 11, Information Healthcare Press, New York (2009).

Brittain, "Profiles of Drug Substances, Excipients, and Related Methodology," Journal of Pharmaceutical Physics, vol. 12, Elsevier Academic Press, Amsterdam (2010).

(56) References Cited

OTHER PUBLICATIONS

Bundgaard, "Novel Chemical Approaches in Prodrug Design," Drugs of the Future, 16:443-458 (1991).
Cai et al., "A humanized UGT1 mouse model expressing the UGT1A1*28 allele for assessing drug clearance by UGT1 A1-dependent glucuronidation," Drug Metab. Dispos., 38:879-886 (2010).
Campbell Roberts et al., "Quantitative analysis of mannitol poly morphs. X-ray powder diffractometry-exploring preferred orientation effects," J. Pharm. Biomed. Anal., 28:1149-1159 (2002).
Cantini et al., "[Fluoxetin combined with cyclobenzaprine in the treatment of fibromyalgia]," Minerva Med., 85:97-100 (1994) (Abstract only).
Cavaljuga et al., "Therapeutic effects of two antidepressant agents in the treatment of posttraumatic stress disorder (PTSD)," Bosn J. Basic Med. Sci. III, 3:12-16 (2003).
Commissiong et al., "Cyclobenzaprine: a possible mechanism of action for its muscle relaxant effect," Can. J. Physicol. Pharmacol., 59:37-44 (1981).
Cotton and Down, "Cyclobenzaprine hydrochloride," Anal Profiles Drug Subs, 17:41-72 (1988).
Davies et al., "Multiple peaking phenomena in pharmacokinetic disposition," Clinical Pharmacokinetics, 49:351-377 (2010).
Descamps et al., "Transformation of pharmaceutical compounds upon milling and comilling: the role of T(g).," J. Pharm. Sci., 96:1398-1407 (2007).
Dobrinska, "Enterohepatic circulation of drugs," J. Clin. Pharmacol., 29:577-580 (1989).
El-Banna et al., "Physicochemical study of drug binary systems. Part 3: Tolbutamide-urea and tolbutamide-mannitol systems," Pharmazie., 30:788-792 (1975).
El-Banna et al., "The application of solid dispersion technique in the preparation of therapeutic tablets. Part 1: Paracetamol, amylobarbitone, and caffeine tablets," Pharmazie, 32:511-515 (1977).
Ereshefsky et al., "Pharmacokinetic factors affecting antidepressant drug clearance and clinical effect: evaluation of doxepin and imipramine—new data and review," Clin. Chem., 34:863-880 (1988).
FDA Guidance for Industry, Bioavailability and Bioequivalence Studies for Orally Administered Drug Products—General Consideration, US Dept. of Health and Human Services, FDA, Center for Drug Evaluation and Research, pp. 1-23 (2003).
Fossaluzza et al., "Combined therapy with cyclobenzaprine and ibuprofen in primary fibromyalgia syndrome," Int. J. Clin. Pharmacol. Res., 12:99-102 (1992).
Fronczek et al., "Three polymorphs (alpha, beta, and delta) of D-mannitol at 100 K," Acta Crystallographica Section C, 59:o567-o570 (2003).
Fujiwara et al., "Developmental hyperbilirubinemia and CNS toxicity in mice humanized with the UDP glucuronosyltransferase 1 (UGT1) locus," Proc. Natl. Acad. Sci, USA, 107:5024-5029 (2010).
Gai et al., "Bioavailability of a controlled-release cyclobenzaprine tablet and influence of a high fat meal on bioavailability," Int. J. Clin. Pharmacol. Ther., 47:269-274 (2009).
Green et al., "Glucuronidation of amine substrates by purified and expressed UDP-glucuronosyltransferase proteins," Drug Metab. Dispos., 26:860-867 (1998).
Guo et al., "Liquid chromatography-tandem mass spectrometry method for measurement of nicotine N-glucuronide: a marker for human UGT2B10 inhibition," J. Pharm. Biomed. Anal., 55:964-971 (2011).
Hawes, "N+-glucuronidation, a common pathway in human metabolism of drugs with a tertiary amine group," Drug Metab. Dispos., 26:830-837 (1998).
Hiller et al., "Retigabine N-glucuronidation and its potential role in enterohepatic circulation," Drug Metab. Dispos., 27:605-612 (1999).
Honda et al, "Tricyclic analogs cyclobenzaprine, amitriptyline and cyproheptadine inhibit the spinal reflex transmission through 5-HT(2) receptors," Eur. J. Pharmacol., 458:91-99 (2003).
Hucker et al., "Metabolism of cyclobenzaprine in the dog," Drug Metab. Dispos., 6:184-192 (1978).
Hucker et al., "Physiological disposition and metabolism of cyclobenzaprine in the rat, dog, rhesus monkey, and man," Drug Metab. Dispos., 6:659-672 (1978).
Hucker et al., "Plasma levels and bioavailability of cyclobenzaprine in human subjects," J. Clin. Pharmacol., 17:719-727 (1977).
Jorgensen et al., "Pharmacokinetics of amitriptyline infused intravenously in man," Eur. J. Clin. Pharmacol., 10:337-341 (1976).
Kaivosaari et al., "N-glucuronidation of drugs and other xenobiotics by human and animal UDP-glucuronosyltransferases," Xenobiotica., 41:652-669 (2011).
Katz and Dube, "Cyclobenzaprine in the treatment of acute muscle spasm: review of a decade of clinical experience," Clinical Therapeutics, 10:216-228 (1988).
Kobayashi et al., "Cyclobenzaprine, a centrally acting muscle relaxant, acts on descending serotonergic systems," Eur. J. Pharmacol., 311:29-35 (1996).
Kornhuber et al., "Identification of new functional inhibitors of acid sphingomyelinase using a structure-property-activity relation model," J. Med. Chem., 51:219-237 (2008).
Kubo et al., "Improvement of dissolution rate and oral bioavailability of a sparingly water-soluble drug, (+/−)-5-[[2-(2-naphthalenylmethyl)-5-benzoxazolyl]-methyl]-2, 4-thiazolidinedione, in co-ground mixture with D-mannitol," Biol. Pharm. Bull., 20:460-463 (1997).
Lee et al., "Transinactivation of the epidermal growth factor receptor tyrosine kinase and focal adhesion kinase phosphorylation by dietary flavonoids: effect on invasive potential of human carcinoma cells," Biochem. Pharmacol., 67:2103-2114 (2004).
Link et al., "Cardiovascular regulation in mice lacking alpha2-adrenergic receptor subtypes b and c," Science, 273:803-805 (1996).
Miles et al., "An investigation of human and rat liver microsomal mycophenolic acid glucuronidation: evidence for a principal role of UGT1A enzymes and species differences in UGT1A specificity," Drug Metab. Dispos., 33:1513-1520 (2005).
Moldofsky et al., "Effects of bedtime very low dose cyclobenzaprine on symptoms and sleep physiology in patients with fibromyalgia syndrome: a double-blind randomized placebo-controlled study," J. Rheum., 38:2653-2663 (2011).
Narang and Sherma, "Sublingual mucosa as a route for systemic drug delivery," Int. J. Pharma., Sci., 3:18-22 (2011).
Ohshima et al., "Tissue distribution and metabolism of amitriptyline after repeated administration in rats," Drug Metab. Dispos., 22:21-25 (1994).
Overo et al., "Kinetics of nortriptyline in man according to a two compartment model," Eur. J. Clin. Pharmacol., 8:343-347 (1975).
Protocol Registration Receipt Jun. 26, 2012, "Comparative Bioavailability of sublingual TNX-102, Oral and Intravenous Cyclobenzaprine in Healthy Adults." ClinicalTrials.gov (2012).
Razaghi et al., "Investigation of cyclobenzaprine hydrochloride release from oral osmotic delivery systems containing a water-swellable polymer," Drug Dev. Ind. Pharma., 28:631-639 (2002).
Rizzi et al.,"Cyclic alternating pattern: a new marker of sleep alteration in patients with fibromyalgia?," J. Rheumatol., 31:1193-1199 (2004).
Rosa et al., "Automatic detection of cyclic alternating pattern (CAP) sequences in sleep: preliminary results," 110:585-592 (1999).
Shukla et al., "Mouth Dissolving Tablets I: An Overview of Formulation," Technology Scientia Pharmaceutica, 77:309-326 (2009).
Siddegowda et al., "Cyclo-benzaprinium chloride," Acta Crystallogr Sect E Struct Rep Online. Jul. 1, 2011; 67(Pt 7): o1846 (Abstract only).
Singh et al., "Tablet disintegrants: an overview," American Journal of Pharmtech Research, 2:14-23 (2012).
Sutfin et al., "The analysis and disposition of imipramine and its active metabolites in man," Psychopharmacology, 82:310-317 (1984).
Telang et al., "Crystallization of D-mannitol in binary mixtures with NaCl: phase diagram and polymorphism," Pharm. Res., 20:1939-1945 (2003).
Terzano et al., "Atlas, rules, and recording techniques for the scoring of cyclic alternating pattern sleep," Sleep Med., 3:187-199 (2002).

(56) References Cited

OTHER PUBLICATIONS

Terzano et al., "Polysomnographic analysis of arousal responses in obstructive sleep apnea syndrome by means of the cyclic alternating pattern," J. Clin. Neurophysiol., 13:145-155 (1996).
Thomas et al., "Sleep as a window into the world of fibromyalgia syndrome," J. Rheumatol., 38:2499-2500 (2011).
Till et al., "Evidence for route dependent biotransformation of cyclobenzaprine hydrochloride," Biopharm. Drug Dispos., 3:19-28 (1982).
Tukey et al., "Human UDP-glucuronosyltransferases: metabolism, expression, and disease," Annu. Rev. Pharmacol. Toxicol., 40:581-616 (2000).
Vaddady et al., "In vitro pharmacokinetic/pharmacodynamic models in anti-infective drug development: focus on TB," Future Med. Chem., 2:1355-1369 (2010).
Wang et al., "Identification of human liver cytochrome P450 isoforms involved in the in vitro metabolism of cyclobenzaprine," Drug Metab. Dispos., 24:786-791 (1996).
Way et al., "Isotope dilution gas chromatographic-mass spectrometric measurement of tricyclic antidepressant drugs. Utility of the 4-carbethoxyhexafluorobutyryl derivatives of secondary amines," J. Anal. Toxicol., 22:374-382 (1998).
Weaver et al., "An instrument to measure functional status outcomes for disorders of excessive sleepiness," Sleep, 20(10):835-43 (1997).
Winchell et al., "Cyclobenzaprine pharmacokinetics, including the effects of age, gender, and hepatic insufficiency," J. Clinical Pharmacol., 42:61-69 (2002).
Wong et al., "Potential interference of cyclobenzaprine and norcyclobenzaprine with HPLC measurement of amitriptyline and nortriptyline: resolution by GC-MS analysis," J. Anal. Toxicol., 19:218-224 (1995).
Yan et al., "Absolute bioavailability and stereoselective pharmacokinetics of doxepin," Xenobiotica., 32:615-623 (2002).
Zajc et al., "Physical properties and dissolution behaviour of nifedipine/mannitol solid dispersions prepared by hot melt method," Int. J. Pharm., 291:51-58 (2005).
Zelapar Full Prescribing Information, Cardinal Health, Inc., Valeant Pharmaceuticals North America (2006).
Grof et al., "Preliminary Comparative trial of proheptatriene and imipramine in the treatement of depressions. (An intensive and controlled study)," Activitas Nervosa Superior, 7:288-289 (1965).
Vinar et al., "Proheptatriene in depression (extensive study)," Activitas Nervosa Superior, 7:290 (1965).
Caillé et al., "Pharmacokinetics of two lorazepam formulations, oral and sublingual, after multiple doses," Biopharmaceutics and Drug Disposition, 4(1):31-42 (1983).
Cyclobenzaprine (Flexeril), eMedEXpert.com—Facts, Oct. 5, 2008 (Oct. 5, 2008), pp. 1-2, XP055239326,Retrieved from the Internet: URL:http://www.emedexpert.com/facts/cyclobenzaprine-facts.shtml [retrieved on Jan. 7, 2016].
Fibromyalgia: medications for fibromyalgia. Jun. 12, 2008 (3 pages) Tricyclic anti-depressants. May be obtained from the Wayback Machine at https://web.archive.org/web/20080612014615/http://www.spinehealth.com/conditions/fibromyalgia/fibromyalgia-medications-fibromyalgia.
Price et al., "Single-dose pharmacokinetics of sublingual versus oral administration of micronized 17 beta-estradiol," Obstetrics and Gynecology, 89(3):340-345 (1997).
RX-s.net Retrieved from the Internet: URL:https://web.archive.org/web/20060516153148/http:1/rx-s.net/weblog/more/cyclobenzaprine_flexerilreg/ [retrieved on Mar. 12, 2013], from 2006 (2 pages).
Ford et al., "Thermal Analysis of Sulphamethoxazole—Sugar Physical Mixes," Drug Development and Industrial Pharmacy, 11(5):1111-1112 (1985).
Carette et al., "Compatison of amitriptyline, cyclobenzaprine, and placebo in the treatment of fibromyalgia. A randomized, double-blind clinical trial," Arthritis & Rheumatism, 37(1):32-40 (1994).
Higashi et al., "Validation of the hospital anxiety and depression scale in a gastro-intestinal clinic," Japanese Journal of Gastroenterologieal Surgery, 93(12):884-892 (1996).

Miller et al., "Management of fibromyalgia, a distinct rheumatologic syndrome," Clinical Pharmacy, 6(10):778-786 (1987).
Bennett et al., "A comparison of cyclobenzaprine and placebo in the management of fibrositis: A double-blind controlled study," Arthritis Rheum, 31:1535-1542 (1988).
Walsh, "Drugs Used to Treat Insomnia in 2002: Regulatory-Based Rather than Evidence-Based Medicine," 27(8):1441-1442 (2004)
Bingshen, et al., "Pharmacy of Chinese Materia Medica," Chinese Medicine Science and Technology Publishing House, 384-387 (Feb. 28, 2018) (English Translation).
Calandre et al., "Monotherapy or combination therapy for fibromyalgia treatment?," Current Rheumatology Reports, 14(6):568-575 (2012).
Cimolai, "Cyclobenzaprine: a new look at an old pharmacological agent," Expert Review of Clinical Pharmacology, 2(3):255-263 (2009).
Cipriani, et al., "Comparative efficacy and acceptability of 21 antidepressant drugs for the acute treatment of adults with major depressive disorder: a systematic review and network meta-analysis," Lancet, 391(10182):1358-1366 (2018).
Fietta et al., "Fibromyalgia and psychiatric disorders," Acta Biomed, 78(2):88-95 (2007).
Kerner et al., "Obstructive sleep apnea is linked to depression and cognitive impairment: evidence and potential mechanisms," American Journal of Geriatric Psychiatry, 24(6):496-508 (2016).
Moldofsky et al., "Relationship of sleep quality and fibromyalgia outcomes in a phase 2b randomized, double-blind, placebo-controlled study of bedtime, rapidly absorbed, sublingual cyclobenzaprine (TNX-102 SL)," Arthritis Rheumatology, 67 (suppl 10) (2015).
Pae et al., "The relationship between fibromyalgia and major depressive disorder: a comprehensive review," Current Medical Research and Opinion, 24(8):2359-2371 (2008).
Rosa et al., "Somatic treatments for mood disorders," Neuropsychopharmacology, 37(1):102-116 (2012).
Sura et al., "Prevalence and determinants of anticholinergic medication use in elderly dementia patients," Drugs Aging, 30:837-844 (2013).
Walsh, "Drugs used to treat insomnia in 2002: regulatory-based rather than evidence-based medicine," Sleep, 27(8):1441-1442 (2004).
Way et al., "Isotope dilution gas chromatographic-mass spectrometric measurement of tricyclic antidepressant drugs. Utility of the 4-carbethoxyhexafluorobutyryl derivatives of secondary amines," Journal of Analytical Toxicology, 22:374-382 (1998).
Zhang et al., "Concepts and challenges in quantitative pharmacology and model-based drug development," AAPS J., 10:552-559 (2008).
Zhou et al., "Role of human UGT2B10 in N-glucuronidation of tricyclic antidepressants, amitriptyline, imipramine, clomipramine, and trimipramine," Drug Metab. Dispos., 38:863-870 (2010).
U.S. Appl. No. 13/918,692, filed Jun. 14, 2013, Pending.
U.S. Appl. No. 15/915,688, filed Mar. 8, 2018, Pending.
U.S. Appl. No. 16/518,338, filed Jul. 22, 2019, Pending.
U.S. Appl. No. 17/082,949, filed Oct. 28, 2020, Pending.
U.S. Appl. No. 17/121,547, filed Dec. 14, 2020, Pending.
U.S. Appl. No. 16/215,952, filed Dec. 11, 2018, Pending.
U.S. Appl. No. 17/269,106, filed Feb. 17, 2021, Pending.
Bennet et al., "An internet survey of 2,596 people with fibromyalgia," BMC Musculoskeletal Disorders, 8(27):2-12 (2007).
Bjellanda et al., "The validity of the Hospital Anxiety and Depression Scale. An updated literature review," Journal of Psychosomatic Research, 52:69-77 (2002).
Experimental Report, Batch Number #CYB_GAL_001, dated Aug. 24, 2020 (13 pages).
Gibson, "Pharmaceutical Preformulation and Formulation", 2nd Edition, New York, 231-234 (2009) (8 pages).
Goodnick et al., "Psychotropic treatment of chronic fatigue syndrome and related disorders," Journal of Clinical Psychiatry, 54(1):13-20 (1993).
Harris et al., "Cyclobenzaprine (CBP) is a Potent Antagonist of Serotonin Receptor 2a (5-HT2a) and alpha-2 Adrenergic Receptors: Mechanistic Implications for Promoting Restorative Sleep in Fibromyalgia Syndrome (FMS)," Arthritis & Rheumatism, 62(10S): abstract 799 (2010).

(56) References Cited

OTHER PUBLICATIONS

Hospital Anxiety and Depression Scale Questionnaire (undated) (1 page).
Moldofsky et al., "A double-blind, randomized, parallel study of the safety, efficacy and tolerability of very low-dosage cyclobenzaprine compared to placebo in subjects with Fibromyalgia," Arthritis & Rheumatology, 46(9S):S614 (2002).
Mullin, "Crystallization and Precipitation," Ullman's Encyclopedia of Industrial Chemistry, 6th Edition, vol. 10, London 424-428 (2009) (16 pages).
PTSD, Japanese Journal of Molecular Psychiatry, 2(3):39-45 (2002) (no translation).
Razaghi et al., "Investigation of cyclobenzaprine hydrochloride release from oral osmotic delivery systems containing a water-swellable polymer," Drug Development and Industrial Pharmacy, 28(6):631-639 (2002).
Razaghi et al., "Release of cyclobenzaprine hydrochloride from osmotically rupturable tablets," Drug Development and Industrial Pharmacy, 28(6):695-701 (2002).
Riumachi byougaku text [Rheumatology text], Japan, Shindan to Chiryo Sha, Inc., Sep. 10, 2010, pp. 410-412.
Rowe et al., "Handbook of Pharmaceutical Excipients," 6th Edition, London 424-428 (2009) (7 pages).
Ullmann's Encyclopedia of Industrial Chemistry, 6th Edition, Weinheim, vol. 10, Chapter 2 (16 Pages) (2003).
Alamo et al., "Evaluation of a patient-centred approach in generalized musculoskeletal chronic pain/fibromyalgia patients in primary care," Patient Education and Counseling, 48(1):23-31 (2002).
Anderson et al., "Evidence-based guidelines for treating depressive disorders with antidepressants: A revision of the 2000 British Association for Psychopharrnacology guidelines," Journal of Psychopharmacology, 22(4):343-396 (2008).
Anonymous, "Guideline on clinical investigation of medicinal products in the treatment of depression," European Medical Agency Science Medicines Health, (May 30, 2013) (19 pages).
Bajwa et al., "Low and therapeutic doses of antidepressants are associated with similar response in the context of multimodal treatment of pain," Pain Physician, 12:893-900 (2009).
Caley et al., "SSRI efficacy—finding the right dose," Journal of Psychiatric Practice, 8(1):33-40 (2002).
Carette et al., "Comparison of amitriptyline, cyclobenzaprine, and placebo in the treatment of fibromyalgia. A randomized, double-blind clinical trial," Arthritis and Rheumatism, 37(1):32-40 (1994).
Declaration of Dr. Gregory M. Sullivan, M.D., Summary of results from F304 Trial (Apr. 16, 2021) (2 pages).
European Patent Office Apr. 1, 2022, Written Decision for European Patent Application No. 12755254.5 (33 pages).

Flexeril® (Flexeril (Cyclobenzaprine HCI) Tablets, 2001, C:\N17-821\N17821S045AP1tr.doc (fda.gov)) (9 pages).
Fluoxetine Tables, USP, Aug. 2014 (6 pages).
Jilani et al., Mirtazipine, StatPearls Publishing [Internet] (2021) (6 pages).
Lok et al., "The Performance of the Hospital Anxiety and Depression Scale for Screening of Depressive and Anxiety Disorders in Patients with Rheumatoid Arthritis (RA)," Arthritis and Rheumatology, 62(10S): Abstract 1777 (2010) (2 pages).
*Merck & Co., Inc.* v. *Danbury Pharmacal, Inc.*, Civil Action No. 86-588 MMS, U.S. District Court of Delaware, Opinion (Aug. 31, 1988) (32 pages).
Product monograph for Elavil® Amitriptyline Hydrochloride Tablets USP (Jul. 23, 2010) (17 pages).
Second Declaration of Dr. Gregory M. Sullivan, M.D. (Dec. 21, 2021) (3 pages).
Singer et al., "Hospital anxiety and depression scale cutoff scores for cancer patients in acute care," British Journal of Cancer, 100:908-912 (2009).
Elsner et al., "Newer generation fentanyl transmucosal products for breakthrough pain in opioid-tolerant cancer patients," Clinical Drug Investigation, 31(9): 605-618 (2011).
Hu Xian Feng et al., "Overview of fibromyalgia syndrome treatment," Chinese Medical Journal of Metallurgical Industry, 23(4):454-456(2006) (Machine Translation).
Katz et al., "A study of sublingual absorption. II. Striated muscle relaxants and neurovegetative blocking agents," Journal of the American Pharmaceutical Association, 44(8):472-476 (1955).
Li Xinzhong et al., Handbook of Practical Drug for Residents, the 1st edition, (2009) (Machine Translation).
Shen et al, "The Advance on Studies of Fibromyalgia syndrome," Chinese Journal of Clinical Neurosciences, 20(3):329-334 (2012).
U.S. Appl. No. 17/226,058, filed Apr. 8, 2021, Pending.
U.S. Appl. No. 17/951,723, filed Sep. 23, 2022, Pending.
Li Jianhong, "New Drug Handbook," Jiangxi Science and Technology Press, 2nd Edition, pp. 81-82 (2005) (3 pages) (English Translation).
Mease et al., "Fibromyalgia Syndrome Module at OMERACT 9," Journal ofRheumatology, 36(10):2318-2329 (2009).
Tofferi et al., "Treatment of fibromyalgia with cyclobenzaprine a meta-analysis," Arthritis & Rheumatology, 51(1):9-13 (2004).
U.S. Appl. No. 17/951,723, filed Sep. 23, 2022, Abandoned.
U.S. Appl. No. 16/903,965, filed Jun. 17, 2020, Abandoned.
U.S. Appl. No. 18/385,468, filed Oct. 21, 2023, Pending.
U.S. Appl. No. 18/382,262, filed Oct. 31, 2023, Pending.
U.S. Appl. No. 18/037,815, filed May 19, 2023, Pending.
U.S. Appl. No. 18/212,500, filed Jun. 21, 2023, Pending.

\* cited by examiner

METHODS AND COMPOSITIONS FOR TREATING DEPRESSION USING CYCLOBENZAPRINE

This patent application claims priority from provisional patent application Ser. No. 61/449,838, filed Mar. 7, 2011.

FIELD OF THE INVENTION

The present invention relates to methods for the treatment or prevention of depression, and related pharmaceutical compositions. Of particular interest are pharmaceutical compositions comprising cyclobenzaprine, alone, or in combination with an antidepressant drug.

BACKGROUND OF THE INVENTION

Cyclobenzaprine, or 3-(5H-dibenzo[a,d]cyclohepten-5-ylidene)-N,N-dimethyl-1-propanamine, was first approved by the U.S. Food and Drug Administration in 1977 for the treatment of acute muscle spasms of local origin. (Katz, W., et al., *Cyclobenzaprine in the Treatment of Acute Muscle Spasm: Review of a Decade of Clinical Experience*, Clinical Therapeutics 10:216-228 (1988)). Cyclobenzaprine has also been studied in the treatment of fibromyalgia. In a study of 120 fibromyalgia patients, those receiving cyclobenzaprine (10 to 40 mg) over a 12-week period had significantly improved quality of sleep and pain score. There was also a reduction in the total number of tender points and muscle tightness.

Furthermore, the utility of a very low dose cyclobenzaprine as an agent for improving the quality of sleep, as a sleep deepener, or for treating sleep disturbances has been investigated. The very low dosage regimen was viewed as particularly useful in treating sleep disturbances caused by, exacerbated by or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety or for treating an illness caused by or exacerbated by sleep disturbances, and symptoms of such illness and generalized anxiety disorder. See U.S. Pat. Nos. 6,395,788 and 6,358,944, herein incorporated by reference.

It is important to develop new methods and pharmaceutical compositions that ameliorate depression with minimal side effects.

SUMMARY OF THE INVENTION

In one aspect the invention is a method for treating depression comprising administering to a human in need of such treatment a pharmaceutical composition comprising cyclobenzaprine in a therapeutically effective amount and a therapeutically effective carrier, wherein such treatment ameliorates or eliminates the depression. Typically, the cyclobenzaprine is administered at bedtime. Generally, the dose is less than 5 mg/day. An antidepressant drug may be administered sequentially or concurrently. In a second aspect the invention is a pharmaceutical composition comprising a therapeutically effective amount of cyclobenzaprine in combination with an antidepressant drug.

DETAILED DESCRIPTION OF THE INVENTION

We have discovered that cyclobenzaprine treatment was associated with a significant improvement in the HAD Depression subscore in fibromyalgia patients. The Hospital Anxiety and Depression Scale (HAD) is a widely used patient self-rated scale with 14 questions (7 "anxiety" and 7 "depression" questions) that ranges from 0-42. Therefore, we believe that a low dose cyclobenzaprine will be effective for treating depression, including major depressive disorder. Thus, one aspect the invention is a method for treating depression, including major depressive disorder, using a very low dose of cyclobenzaprine.

"Cyclobenzaprine" includes cyclobenzaprine or a metabolite thereof, prodrug of cyclobenzaprine or a metabolite thereof. Metabolites of cyclobenzaprine useful according to the methods of this invention are metabolites that have substantially the same activity or better as cyclobenzaprine in alleviating depression symptoms. Cyclobenzaprine metabolites that may be useful according to this invention include CBP 10,11-trans-dihydriol, N-desmethyl-2-hydroxycyclobenzaprine, 3-hydroxycyclobenzaprine, N-desmethylcyclobezaprine cyclobenzaprine N-oxide or a chiral isomer of these metabolites. A prodrug of cyclobenzaprine is a derivative of cyclobenzaprine that is metabolized in vivo into the active agent. Prodrugs useful according to this invention are those that have substantially the same activity or better than cyclobenzaprine in treating or preventing the symptoms of depression. Methods for making prodrugs are readily known in the art (e.g., Balant, L. P., *Prodrugs for the Improvement of Drug Absorption Via Different Routes of Administration*, Eur. J. Drug Metab. Pharmacokinet. 15:143-153 (1990); and Bundgaard, H., *Novel Chemical Approaches in Prodrug Design, Drugs of the Future* 16:443-458 (1991); incorporated by reference herein).

As used herein, a "therapeutically effective amount" of cyclobenzaprine for the purposes of this invention refers to the amount of the compound that prevents or alleviates or eliminates depression. A physician can readily determine when symptoms are prevented or alleviated or eliminated, for example through clinical observation of a subject, or through reporting of symptoms by the subject during the course of treatment. One skilled in the art can readily determine an effective amount of a cyclobenzaprine to be administered, by taking into account factors such as the size, weight, age and sex of the subject, the extent of disease penetration or persistence and severity of symptoms, and the route of administration. Generally, a therapeutically effective amount of cyclobenzaprine administered to a subject is between 0.1 mg to about 50 mg/day, between 0.5 to about 10 mg/day, between 1 mg and 5 mg/day, or between 1 and 4 mg/day. Higher or lower doses are also contemplated.

In one embodiment the cyclobenzaprine is administered at a very low dose to minimize side effects observed at higher doses. The low doses include doses of less than 5 mg/day or less than 2.5 mg/day. Even lower doses are also contemplated. Generally, cyclobenzaprine therapy can be carried out indefinitely to alleviate the symptoms of interest and frequency of dosage may be changed to be taken as needed. The period of treatment should be carried out for as long as necessary to alleviate depression symptoms and the cyclobenzaprine administered at night-time and at an appropriate dose. For example, the doses may be 1 mg/day, 2 mg/day, 3 mg/day or 4 mg/day.

In another embodiment of the invention, cyclobenzaprine is administered in combination with a drug which alleviates the symptoms of depression. The drugs may be administered sequentially or concurrently with the cyclobenzaprine. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary selective serotonin reuptake inhibitor or a serotonin-norepinephrine reuptake inhibitor include, but are not limited to, buprorion (at a dose between about 105 mg and 450 mg/day), citalopram (at a dose between about 10 mg and 40 mg/day), desvenlafaxine (at a dose between about 50 mg and 400 mg/day), duloxetine (at a dose between about 40 mg and 120 mg/day), escitalopram (at a dose between about 10 mg and 20 mg/day), fluoxetine (at a dose between about 20 mg and 80 mg/day), fluvoxamine (at a dose between about 100 mg and 300 mg/day), milnacipran (at a dose between about 30 mg and 200 mg/day), paroxetine (at a dose between about 20 mg and 50 mg/day), sertraline (at a dose between about 50 mg and 200 mg/day), tradodone (at a dose between about 150 mg and 600 mg/day), and venlafaxine (at a dose between about 75 mg and 225 mg/day), Exemplary anticonvulsants include, but are not limited to carbamazepine (at a dose between about 400 mg and 1200 mg/day), gabapentin (at a dose between about 900-1800 mg/day), lamotrigine (at a dose between about 100 mg and 400 mg/day), oxcarbazepine (at a dose between about 1200 mg and 2400 mg/day), pregabalin (at a dose between about 150 mg and 600 mg/day), tiagabine (at a dose between about 32 mg and 56 mg/day), topiramate (at a dose between about 200 mg and 400 mg/day), and valproate (at a dose between about 1200 mg and 1500 mg). Exemplary alpha-1-adrenergic receptor antagonists include, but are not limited to, prazosin administered at a dose of between about 0.5 mg to 15 mg/day.

Generally, the amount of cyclobenzaprine in the pharmaceutical composition is between 0.1 mg to about 50 mg, between 0.5 to about 30 mg, or between 1 mg and 20 mg. Higher or lower doses are also contemplated. In one particular embodiment the amount of cyclobenzaprine is very low to minimize side effects observed with higher amounts. The very low amounts are of less than 10 mg or less than 5 mg or less than 2.5 mg. Even lower amounts are also contemplated. In another embodiment of the invention, cyclobenzaprine is combined with a drug which may further alleviate the symptoms of depression. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary anticonvulsants include, but are not limited to carbamazepine (400 mg to 1200 mg), gabapentin (900 mg to 1800 mg), lamotrigine (100 mg to 400 mg), oxcarbazepine (1200 mg to 2400 mg), pregabalin (150 mg to 600 mg), tiagabine (32 mg to 56 mg), topiramate (200 mg to 400 mg), and valproate (1200 mg to 1500 mg). An exemplary alpha-1-adrenergic receptor antagonists includes, but is not limited to, prazosin in the amount of 0.5 mg to 15 mg. An exemplary selective serotonin reuptake inhibitor is escitalopram (in the amount of 10 mg and 20 mg).

Any suitable route of administration may be employed for providing the patient with an effective dosage of cyclobenzaprine. For example, buccal, oral, rectal, parenteral, transdermal, subcutaneous, sublingual, intranasal, intramuscular, intrathecal and the like may be employed as appropriate. The term parenteral as used herein includes subcutaneous, intracutaneous, intravenous, intramuscular, intra-articular, intrasynovial, intrasternal, intrathecal, intralesional and intracranial injection or infusion techniques. Dosage forms include tablets, such as scored tablets, coated tablets, or orally dissolving tablets; thin films, caplets, capsules (e.g. hard gelatin capsules), troches, dragees, dispersions, suspensions, solutions, patches and the like, including sustained release formulations well known in the art. In one preferred embodiment, the dosage form is an orally dissolving tablet or a thin film.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices. Pharmaceutical compositions of the invention for parenteral administration can take the form of an aqueous or nonaqueous solution, dispersion, suspension or emulsion. In preparing pharmaceutical compositions of the invention for parenteral administration, cyclobenzaprine can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of cyclobenzaprine. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the invention for oral administration, cyclobenzaprine can be combined with one or more solid or liquid inactive ingredients to form tablets, capsules, pills, powders, granules or other suitable oral dosage forms. For example, cyclobenzaprine can be combined with at least one pharmaceutically acceptable carrier such as a solvent, filler, binder, humectant, disintegrating agent, solution retarder, absorption accelerator, wetting agent absorbent or lubricating agent. In one embodiment, cyclobenzaprine is combined with carboxymethylcellulose calcium, magnesium stearate, mannitol or starch, and is formed into tablets by conventional tableting methods.

Pharmaceutical compositions of the invention can be formulated so as to provide buccal absorption including thin film formulations and orally dissolving tablets to provide faster absorption than the oral/GI route and to bypass first-pass hepatic metabolism of cyclobenzaprine by cytochrome P-450 3A4 as a CYP3A substrate. Preferably, a controlled-release pharmaceutical composition of the invention is capable of releasing cyclobenzaprine into a subject at a rapid onset, so as to maintain a substantially constant or desired pharmacological activity for a given period of time, reduce or remove the effect of food on absorption, and to provide elimination of the drug and metabolites from the body with a reduced terminal elimination phase.

Pharmaceutical compositions of the invention can also be formulated so as to provide controlled-release of cyclobenzaprine upon administration of the composition to a subject. Preferably, a controlled-release pharmaceutical composition of the invention is capable of releasing cyclobenzaprine into a subject at a desired rate, so as to maintain a substantially constant or desired pharmacological activity for a given period of time. As used herein, a "controlled-release component" is a compound such as a lipid or mixture of lipids, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise cyclobenzaprine and a controlled-release component. As used herein, a "controlled-release component" is a compound such as a polymer, polymer matrix, gel, permeable membrane, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, cyclobenzaprine is incorporated into a sol-gel matrix that is a solid at room temperature. This sol-gel matrix is implanted into a subject having a body temperature high enough to induce gel formation of the sol-gel matrix, thereby releasing the active ingredient into the subject.

In one embodiment, pharmaceutical compositions of the invention may comprise cyclobenzaprine and components that form micelles. Micelles containing cyclobenzaprine in the stomach and proximal small intestine facilitate absorption. Example of a micelle-component which is activated by exposure to a certain temperature is found in U.S. Pat. Nos. 6,761,903; 6,720,001; 6,383,471; 6,309,663; 6,267,985; and 6,248,363, incorporated herein by reference. In this embodiment, cyclobenzaprine is incorporated into a soft-gel capsule. Such components may mimic the augmentation of absorption termed the "food effect", and such formulations may provide more predictable absorption by eliminating the "food effect" from dietary sources.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The magnitude of a prophylactic or therapeutic dose of the active ingredient (i.e., cyclobenzaprine or metabolite thereof) in the prevention or treatment of a human will vary with the type of affliction, the severity of the patient's affliction and the route of administration. The dose and dose frequency will also vary according to the age, weight and response of the individual patient. However, the dosage will not equal or exceed 5 mgs per day. In a preferred embodiment, one dose is given at bed time or up to several hours before bedtime to facilitate the achievement of deep, refreshing sleep. Bedtime may be any hour of the day at which a person engages in the most extensive period of sleep.

Any of the methods of treatment described above may be combined with psychotherapeutic intervention to improve the outcome of the treatment. Of particular interest is psychotherapeutic intervention directed at improvement in terms of reducing depression.

A pharmacogenomic test to measure cytochrome CYP3A4, CYP1A2, CYP3A and CYP2G6 may be used to predict the metabolism of cyclobenzaprine by certain patients in personalized medicine. Thus, the invention is a method for selecting an effective dose of cyclobenzaprine to be administered to a human in need of such treatment to correct for variations in cyclobenzaprine metabolism. The method comprises obtaining a genetic sample from said human and identifying the CYP1A2, CYP3A4, CYP3A or CYP2G6 genotype of said human, for example by using a gene chip or a PCR technique, to identify the alleles of one or more of the genes. Different alleles metabolize cyclobenzaprine at different speeds. For individuals having a cytochrome allele identified to metabolize cyclobenzaprine quickly a higher dose of cyclobezaprine is administered. For individuals having an allele identified to metabolize cyclobenzaprine slowly a lower dose of cyclobenzaprine is administered. The genetic test can be sold as a kit with the product to physicians/lab testing services.

In order that this invention to be more fully understood, the following examples are set forth. These examples are for the purpose of illustration only and are not to be construed as limiting the scope of the invention in any way. The practice of the invention is illustrated by the following non-limiting examples.

EXAMPLES

Example 1

Tablet Formulation

A typical oral formulation for coated tablets consists of the following: Formula quantity per tablet (mg.) cyclobenzaprine 1.0, lactose 74.0, corn starch 35.0, water (per thousand tablets) 30.0 ml, magnesium stearate 1.0, corn starch 25.0 The active ingredient (cyclobenzaprine) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration.

Tablets are coated by standard aqueous or nonaqueous techniques. For example, 2.5 mg of hydroxypropymethylcellulose can be dissolved in 25 mg of deionized water. An aqueous (10 mg) suspension of 1.88 mg talc, 0.5 mg of titanium dioxide, 0.1 mg of yellow iron oxide, and 0.02 mg of red iron oxide is stirred into this solution. The coating suspension is sprayed on the tablets and the coated tablets are dried overnight at 45 degree C.

Example 2

Development of an Optimized Gelcap Formulation of VLD Cyclo for Depression

We are developing a novel gelcap (KRL103) that employs a specific mixture of lipids to form micelles containing cyclobenzaprine that is expected to speed upper GI absorption, increase efficiency of absorption (in stomach and proximal small intestine); decrease or eliminate food effect (which is 20% for the Amrix formulation of cyclobenzaprine) and speed elimination (since lower GI absorption may prolong the terminal elimination phase in existing formulations). The gelcap formulation is expected to result in increased dosage precision; decreased potential for morning "hangover"; and potentially more rapid induction of sleep.

Example 3

Treatment of Depression

Of 37 patients with fibromyalgia (American College of Rheumatology (ACR), 1990 criteria) in the screened population, 36 were randomized and 33 completed this 8-week, double-blind, placebo-controlled, dose-escalating study of very low dose cyclobenzaprine (VLD CBP) 1-4 mg at bedtime. We evaluated changes in subjective symptoms and objective sleep measures in the treated population (n=36) including: pain, tenderness (dolorimetry), fatigue, mood [Hospital Anxiety and Depression Scale (HAD)] and EEG sleep physiology (at screening, baseline and weeks 2, 4 and 8).

Hospital Anxiety and Depression Scale (HAD). The Hospital Anxiety and Depression Scale (HAD) is a widely used patient self-rated scale with 14 questions (7 "anxiety" and 7 "depression" questions) that ranges from 0-42. For subjects who received VLD CBP, the HAD score changed from 13.7 at baseline to 10.4 at week 8, which was a decrease (or improvement) of 3.3 (24.1%, p=0.012). In contrast, placebo treatment did not result in statistically significant changes in HAD scale, which was 15.7 at baseline and 15.1 at week 8 (−3.8%, p=0.459). Comparison of the change from baseline between the VLD CBP and placebo groups at week 8 did not reveal a significant effect of VLD CBP treatment on the HAD scale.

The HAD Depression Subscale score was also analyzed. For subjects who received VLD CBP, the HAD depression subscale changed from 6.3 at baseline to 4.9 at week 8, which was a decrease (or improvement) of 1.4 (22.2%, p=0.017). In contrast, placebo treatment did not result in statistically significant changes in intragroup HAD depression subscale, from 6.7 at baseline to 7.4 at week 8, which was an increase of 0.7 (10.4%, p=0.319). Comparison of the change from baseline between the VLD CBP and placebo groups at week 8 revealed that VLD CBP treatment was associated with a significant improvement in the HAD Depression subscore (p=0.023).

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

I claim:

1. A method for treating a major depressive disorder in a fibromyalgia patient in need thereof, the method comprising administering to the fibromyalgia patient a pharmaceutical composition comprising cyclobenzaprine or a pharmaceutically acceptable or water-soluble salt thereof and a pharmaceutically acceptable carrier, wherein treatment with the cyclobenzaprine or salt thereof ameliorates or eliminates the major depressive disorder, and wherein the amount of cyclobenzaprine administered is less than 5 mg/day.

2. The method of claim 1, wherein the amount of cyclobenzaprine administered is less than 2.5 mg/day.

3. The method of claim 1, wherein the method further comprises administering the pharmaceutical composition sequentially or concurrently with an antidepressant drug.

4. The method of claim 1, wherein the pharmaceutical composition is administered as an orally dissolving tablet or as a thin film formulation.

5. The method of claim 1, wherein the pharmaceutical composition is administered in combination with psychotherapeutic intervention.

6. The method of claim 1, wherein the pharmaceutical composition is administered at bedtime.

* * * * *